(12) United States Patent
Luecke et al.

(10) Patent No.: US 9,051,286 B2
(45) Date of Patent: Jun. 9, 2015

(54) CHLOROHYDRIN PROCESSING EQUIPMENT COMPRISING STAINLESS STEEL

(75) Inventors: Karsten Luecke, Buxtehude (DE); Eckhard Goertz, Hollern (DE); Holger Baer, Weidenring (DE)

(73) Assignee: Dow Global Technologies LLC, Midland, MI (US)

( * ) Notice: Subject to any disclaimer, the term of this patent is extended or adjusted under 35 U.S.C. 154(b) by 145 days.

(21) Appl. No.: 13/810,695

(22) PCT Filed: Jun. 28, 2011

(86) PCT No.: PCT/US2011/042135
§ 371 (c)(1),
(2), (4) Date: Jan. 17, 2013

(87) PCT Pub. No.: WO2012/015553
PCT Pub. Date: Feb. 2, 2012

(65) Prior Publication Data
US 2013/0116452 A1  May 9, 2013

Related U.S. Application Data

(60) Provisional application No. 61/368,578, filed on Jul. 28, 2010.

(51) Int. Cl.
C07D 301/26 (2006.01)
C07D 301/03 (2006.01)
C22C 38/00 (2006.01)
C22C 38/44 (2006.01)
F28F 21/08 (2006.01)

(52) U.S. Cl.
CPC ............ *C07D 301/03* (2013.01); *C07D 301/26* (2013.01); *C22C 38/001* (2013.01); *C22C 38/44* (2013.01); *F28F 21/083* (2013.01)

(58) Field of Classification Search
CPC .......................... C07D 301/26; C07D 301/03
See application file for complete search history.

(56) References Cited

U.S. PATENT DOCUMENTS

| 4,567,303 | A | 1/1986 | Boettger |
| 7,482,496 | B2 | 1/2009 | Hassan |
| 7,906,691 | B2 | 3/2011 | Krafft |

FOREIGN PATENT DOCUMENTS

EP  0368656 A2  5/1990

OTHER PUBLICATIONS

Ahmad, et al., "Corrosion Behavior of Some Stainless Steels in Chlorinated Gulf Seawater", Journal of Applied Electrochemistry, Sep. 2001, pp. 1009-1016, 31(9).
PCT/US2011/042135, Search Report and Written Opinion, mailed Nov. 22, 2011.
Richaud-Minier H. et al., "Titanium and super stainless steel welded tubing solutions for sea water cooled heat exchangers", Materials Technology, Jan. 1, 2009, 10pp, vol. 24, No. 3.
Wallen et al., "Avesta 654 SMO—a new, high molybdenum, high nitrogen stainless steel", Scan. Corros, Congr. Eurocorr '92, 12th, Jan. 1, 1992, 81-90 vol. 1.

*Primary Examiner* — Sun Jae Yoo
(74) *Attorney, Agent, or Firm* — Duane C. Ulmer; KSJLaw, LLC

(57) ABSTRACT

The present invention provides a process for the production of chlorohydrins, comprising generating a chlorohydrins processing stream and contacting at least a portion of a surface comprising a austenitic stainless steel with the chlorohydrin processing stream. It has now been surprisingly discovered that certain stainless steels can be utilized to form portions, or the entirety of, one or more pieces of processing equipment utilized in such processes.

13 Claims, 6 Drawing Sheets

CHLOROHYDRIN PROCESSING EQUIPMENT COMPRISING STAINLESS STEEL

FIELD

The present invention relates to chlorohydrin processing equipment comprising stainless steel.

BACKGROUND

Many chemical processes involve or create challenging environments. In order to operate optimally, or even acceptably, equipment used in such processes must be comprised of materials capable of withstanding the harsh conditions within which it is expected to operate. In particular, processes involving extreme temperatures, pH, and salt and/or halide concentrations may typically employ equipment based in whole or in part on enameled steel, graphite, or titanium in order to obtain the desired equipment performance and/or lifetime.

For example, the production of chlorohydrins may typically generate process and/or waste streams comprising concentrations of halogenated byproducts and/or chloride salts that may be corrosive to equipment comprised of non-specialized materials like carbon, steel and many grades of stainless steel. Degradation or fouling of process equipment can not only be inefficient in time and cost aspects, but also, can result in contamination of the desired product(s). Unfortunately, the use of specialized materials such as graphite, titanium or hastelloy and/or materials provided with protective coatings, such as enameled or glass-lined steel, in such processes can be cost prohibitive.

It would thus be desirable to provide chemical processing equipment comprising non-specialized materials and/or materials not provided with protective coatings that could yet withstand the harsh processing conditions created in many chemical processes. In particular, such equipment could be particularly advantageously utilized in processes that generate or include high pH, high salt, and/or high oxidation potential process streams, such as those utilized and/or created in the production of chlorohydrins.

BRIEF DESCRIPTION

The present invention provides a process for the production of chlorohydrins, wherein at least a portion of a surface contacted by a chlorohydrin processing stream comprises a stainless steel. More particularly, the present processes for the production of chlorohydrins can involve process streams, i.e., streams of reactants, products, byproducts, diluents, contaminants or any other component introduced into, and/or generated by, the process, that have one or more of high salt content, high pH, high oxidation potential and/or elevated temperature. It has now been surprisingly discovered that certain stainless steels can be utilized to form portions, or the entirety of, one or more pieces of processing equipment utilized in such processes.

In one aspect, the present invention provides a process for the production of a chlorohydrin. The process comprises generating a chlorohydrin process stream and contacting at least a portion of a surface comprising an austenitic stainless steel with the process stream. The stainless steel comprises from about 0.18 wt % to about 0.52 wt % nitrogen, from about 19.5 wt % to about 24.5 wt % chromium, from about 17.5 wt % to about 22.5 wt % nickel, from about 6.0 wt % to about 7.5 wt % molybdenum, from about 0.01 wt % to about 0.02 wt % carbon, with the remainder being incidental impurities and the balance iron.

In some embodiments, the stainless steel comprises from about 0.18 wt % to about 0.22 wt % nitrogen, from about 23.5 wt % to about 24.5 wt % chromium, from about 21.5 wt % to about 22.5 wt % nickel, from about 6.0 wt % to about 6.5 wt % molybdenum, and from about 0.01 wt % to about 0.02 wt % carbon. In other embodiments, the stainless steel comprises from about 0.48 wt % to about 0.52 wt % nitrogen, from about 19.5 wt % to about 20.5 wt % chromium, from about 17.5 wt % to about 18.5 wt % nickel, from about 7.1 wt % to about 7.5 wt % molybdenum, and from about 0.01 wt % to about 0.02 wt % carbon.

The process stream may have a pH of greater than about 9, or greater than about 10, or even greater than about 11; a salt concentration of at least about 5 wt %, or at least about 10 wt %, or even up to about 20 wt %; a temperature of at least about 70° C., or at least about 80° C., or up to about 90° C.; and/or an oxidation potential of up to about 100 mV/Ag-AgCl, or up to about 200 mV/Ag-AgCl, or even up to about 300 mV/Ag-AgCl. The process stream may comprise any stream introduced and/or generated by the process, and in some embodiments, may comprise a waste stream.

The stainless steel may be a portion of a surface of any processing apparatus utilized in the production of chlorohydrins, including e.g., a conduit, reactor, heat exchanger, separation apparatus, chiller, pump, and the like or combinations of these. In some embodiments, the stainless steel may be a portion of a surface of a separation apparatus, such as a distillation column or a dividing wall column. In other embodiments, the stainless steel comprises at least a portion of a surface of a heat exchanger.

The process can be used in any method for the production of chlorohydrins. In some embodiments, the chlorohydrin produced is epichlorohydrin. In some embodiments, the epichlorohydrin is produced by reacting allyl chloride with chlorine in the presence of water to form glycerol dichlorohydrin (2,3-propylene dichlorohydrin) and treating the glycerol dichlorohydrin with a base to provide the epichlorohydrin. In others, the epichlorohydrin is produced by reacting glycerol with hydrochloric acid to form glycerol dichlorohydrin and treating the glycerol dichlorohydrin with a base to provide the epichlorohydrin. In yet others, the epichlorohydrin is produced by reacting allylalcohol dissolved in hydrochloric acid solution with gaseous chlorine to form glycerol dichlorohydrin and treating the glycerol dichlorohydrin with a base to provide the epichlorohydrin.

The cost savings provided by the use of stainless steel as a substitute for other more expensive materials in the chlorohydrin process are a significant advantage to the present processes themselves, but this advantage can be even further leveraged by use of the chlorohydrins produced thereby to produce additional products. And so, in another aspect, the present invention provides a process for the production of a downstream product using a chlorohydrin produced utilizing the process described herein. For example, the chlorohydrins produced according to the processes described herein can be utilized to produce alkylene oxides, such as propylene oxide or butylene oxide or epichlorohydrin. The alkylene oxides or epoxides produced may, in turn, be utilized to produce glycols, polyols, epoxy resins or synthetic glycerol.

BRIEF DESCRIPTION OF THE DRAWINGS

These and other features, aspects, and advantages of the present invention will become better understood when the following detailed description is read with reference to the accompanying drawings, wherein.

DETAILED DESCRIPTION

Figure 1:
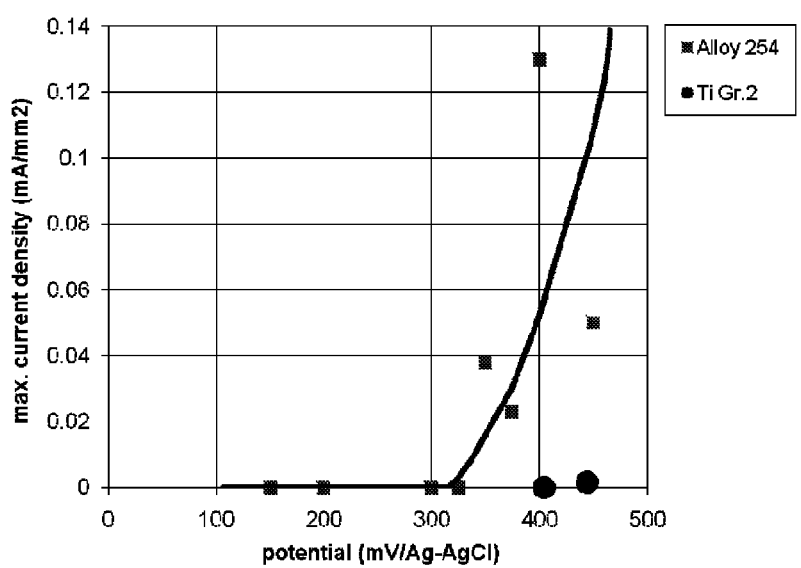
FIG. 1 is a graphical depiction of the effect of applied potentials on crevice corrosion current densities of 254 SMO and grade 2 titanium in 5 wt % salt solution.

The present specification provides certain definitions and methods to better define the present invention and to guide those of ordinary skill in the art in the practice of the present invention. Provision, or lack of the provision, of a definition for a particular term or phrase is not meant to signify any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). Unless otherwise defined, all percents are provided as weight percents.

The present invention provides a process for the production of chlorohydrins, wherein at least a portion of a surface contacted by a chlorohydrin processing stream comprises a stainless steel. That is, it has now been surprisingly discovered that certain stainless steels can be utilized to form portions, or the entirety of, one or more pieces of processing equipment utilized in the production of chlorohydrins. While these stainless steels had previously been reported to be generically useful in chemical processing equipment, their suitability for use in equipment for the production of chlorohydrins is surprising and unexpected due to the extreme conditions that may be present and/or generated by such processes.

More particularly, processes for the production of chlorohydrins can involve process streams, i.e., streams of reactants, products, byproducts, diluents, contaminants or any other component introduced into, and/or generated by, the process, that have one or more of high salt content, high pH, elevated temperature and/or high oxidation potential. That is, salt concentrations of about 0.5 wt %, based upon the total weight of the process stream, or up to about 1.0 wt %, or about 1.5 wt %, or about 2 wt %, or about 2.5 wt %, or about 5 wt %, or about 10 wt %, or even up to about 20 wt %, may typically be introduced into, or generated by, chlorohydrin processes. Further, process streams introduced into, or generated by, chlorohydrin processes may typically have pH values of at least about 8, or about 8.5, or greater than about 9, or 9.5, or 10, or 10.5, or even greater than about 11. Temperatures of at least about 65° C., or about 70° C., or about 75° C., or about 80° C., or about 85° C. or even up to about 90° C. can be generated or used by processes for the production of chlorohydrins.

And so, the stainless steels identified for use in chlorohydrin processing equipment will desirably exhibit a high corrosion resistance, including resistance to crevice corrosion, when exposed to such conditions. That is, the stainless steel utilized will desirably exhibit substantially no current density, i.e., a current density of less than about 0.02 mA/mm$^2$, or less than 0.01 mA/mm$^2$, or even less than about 0.005 mA/mm$^2$, at applied potentials of up to about 100 mV/Ag-AgCl, or up to about 150 mV/Ag-AgCl, or up to about 200 mV/Ag-AgCl, or up to about 250 mV/Ag-AgCl, or even up to about 300 mV/Ag-AgCl when in contact with a processing stream comprising at least about 5 wt % salt, or up to about 10 wt % salt, or even up to about 20 wt % salt.

The stainless steels will further desirably be commercially available in an easily manipulated format, e.g., as thin sheets, suitably used in the manufacture of the desired piece of processing equipment. In some embodiments, the stainless steel utilized will also desirably exhibit sufficient heat conductivity so as to be useful in the formation of heat exchangers used to recover some of the heat present in chlorohydrin processing streams.

It has now been surprisingly discovered that certain highly alloyed austenitic ferritic stainless steels may be utilized in such processes. Preferred stainless steels may have high contents of chromium, nickel, molybdenum and nitrogen and typically may comprise from about 0.18 wt % to about 0.52 wt % nitrogen, from about 19.5 wt % to about 24.5 wt % chromium, from about 17.5 wt % to about 22.5 wt % nickel, from about 6.0 wt % to about 7.5 wt % molybdenum, from about 0.01 wt % to about 0.02 wt % carbon, with the remainder being incidental impurities and the balance iron. Commercially available examples of such stainless steels include, but are not limited to, 904L, 254 SMO® and 654 SMO®. Any of these are advantageously much less costly than nickel-based alloys, or titanium, which may have been used in conventional chlorohydrin processing equipment.

The stainless steel may comprise at least a portion of at least one surface that comes into contact with a process stream in a chlorohydrin process. Such a surface may be a portion of any apparatus commonly used in a chlorohydrins process, such as, e.g., a conduit, reactor, heat exchanger, separation apparatus, chiller, pumps, etc. In some embodiments, the stainless steel may comprise at least a portion of a surface of a separation apparatus, such as a distillation column or dividing wall column.

In particularly advantageous embodiments, the surface may be a portion of an apparatus that comes into contact with a high temperature high turbulence flow of the process stream, since these conditions are optimal for corrosion, and in particular crevice corrosion, to occur. Such conditions are typical within heat exchangers, and the stainless steel can thus advantageously be used in at least a portion of a surface thereof. In such embodiments, the heat conductivity of the stainless steel may be used to absorb/recover some of the heat present in chlorohydrin processing streams.

The stainless steel used may advantageously be commercially available in an easily manipulated formatted, such as thin sheets, so as to be capable of being welded or machined by those of ordinary skill in the machining art to form the desired piece of processing equipment. Each of 904L, 254 SMO® and 654 SMO® are commercially available as thin sheets from, e.g., AvestaPolarit, Schaumberg, Ill., and exhibit sufficient ductility or weldability so as to be readily formed into the desired piece of processing equipment. In those embodiments wherein the stainless steel is desirably utilized to provide at least a portion of a heat exchanger, heat exchangers comprising the stainless steel are commercially available from Alfa Laval, Lund, Sweden.

Whatever the desired piece of processing equipment, it may advantageously be utilized in any of the many known processes for the production of chlorohydrins. For example, olefin chlorohydrins are typically prepared by reacting an olefin with chlorine in the presence of water. The process is believed to occur by means of an intermediate chloronium ion which reacts with the water to form an olefin chlorohydrin. The olefin may be one containing from 2 to about 30 carbon atoms. Alternatively, functionalized olefins, such as allylic compounds including chlorinated-olefins or alcohols, can be used as feed-stock for a chlorohydrin process. For example, 3-chloropropene (allyl chloride) or allylalcohol reacts with chlorine in the presence of water, such as may be provided in the form of aqueous HCl solution to form glycerol dichlorohydrin, which may be treated with a base, such as sodium hydroxide, to provide epichlorohydrin. The process may alternatively include a water miscible solvent, and in such embodiments, the reaction would entail the addition of the hypochlorous acid to a long chain olefin in the presence of water in the water immiscible solvent. Suitable water immiscible solvents include decane, chloroform, and petroleum ethers.

Other processes for producing chlorohydrins involve reacting olefins with hypochlorous acid, wherein the process requires acidifying the olefin with gaseous hydrochloric acid and carrying out the process at a pH of between about 2 to about 7, preferably between about 5 and 6. Alternatively, the preparation of chlorohydrins may be achieved by reaction of olefins with trichloroisocyanuric acid in alcohols, acetic acid or aqueous acetone. Various other methods of forming chlorohydrins are also well known and include reaction olefins with t-butyl hypochlorite or hypochlorous acid substantially free of chloride ions.

Another method of making chlorohydrins involves preparing hypochlorous acid by reacting chlorine and water in the presence of alkaline earth metal hydroxides then, reacting the hypochlorous acid mixture with a vinyl group-containing compound. Yet another route for the preparation of chlorohydrins involves the reaction of glycerine with aqueous or gaseous hydrochloric acid in the presence of water.

The stainless steel surface may be utilized in any of the above processes, or in any process for the production of chlorohydrins known to those of ordinary skill in the art. In preferred embodiments, the chlorohydrin produced is epichlorohydrin, and the stainless steel is a portion of a surface utilized in a chlorohydrin process comprising the reaction of allylchloride with chlorine in the presence of water to form glycerol dichlorohydrin, and the treatment of the glycerol dichlorohydrin with sodium hydroxide to provide epichlorohydrin. In other preferred embodiments, the epichlorohydrin is produced by reacting glycerol with hydrochloric acid to form glycerol-dichlorohydrin and treating the glycerol dichlorohydrin with a base to provide the epichlorohydrin. In yet others, the epichlorohydrin is produced by reacting allylalcohol dissolved in hydrochloric acid with gaseous chlorine to form glycerol dichlorohydrin and treating the glycerol dichlorohydrin with a base to provide the epichlorohydrin.

The cost savings provided by the use of stainless steel as a substitute for other, more expensive, materials in the chlorohydrin process are a significant advantage to the process itself, but can be further leveraged by use of the chlorohydrins produced thereby to produce additional products. For example, propylene chlorohydrin and butylene chlorohydrins are used in producing propylene oxide and butylene oxide, respectively. Epichlorohydrin can be further processed to provide epoxy resins by reaction with bisphenol-A or bisphenol-F, examples of which include those commercially available under the tradename D.E.R.™ and D.E.N™ from the Dow Chemical Company, Midland, Mich. Epichlorohydrin can also be used in the production of synthetic glycerol.

The following examples are set forth for the purpose of illustrating the invention; but these examples are not intended to limit the invention in any manner. One skilled in the art will recognize a variety of substitutions and modifications of the examples that will fall within the scope of the invention.

EXAMPLE 1

The crevice corrosion behavior of the alloy 254 SMO® and titanium (grade 2) in 5 wt % salt solution are compared as follows. The samples are ground with 800 grit silicon carbide paper and rinsed with distilled water prior to testing. The prepped samples are tested in a laboratory crevice corrosion cell with a PTFE gasket providing a 7 mm diameter test surface of the material to be tested. The test cell is then submerged in 1 liter of waste water from a chlorohydrin process, i.e., a solution having an NaCl concentration of 5 wt % at a temperature of between about 74° C. and about 81° C. and a pH of between about 11 and 12. Fluid motion of about 2 m/s is provided by a magnetic stirrer. Potentiostatic corrosion current density measurements at 150, 200, 300, 325, 350, 400 and 450 mV/Ag-AgCl were carried out for a time period of 1 hour. The results from this Example are summarized in FIG. 1.

As shown, 254 SMO® exhibited no corrosion, i.e., exhibited a maximum current density ($mA/mm^2$) of approximately 0, up to an applied potential of about 325 mV/Ag-AgCl, while grade 2 titanium exhibited a current density of 0 up to an applied potential of about 450 mV/Ag-AgCl. This example thus shows that 254 SMO® is a suitable substitute for grade 2 titanium in applications wherein the 254 SMO® will be exposed to conditions including a pH of from about 11 to about 12, a temperature of from about 70° C. to about 85° C. and oxidation potentials of up to about 325 mV/Ag-AgCl.

EXAMPLE 2

The crevice corrosion behavior of the alloy 254 SMO® in 10 wt % and 20 wt % salt solution are evaluated as follows. The samples are ground with 800 grit silicon carbide paper and rinsed with distilled water prior to testing. The prepped samples are tested in a laboratory crevice corrosion cell with a PTFE gasket providing a 7 mm diameter test surface of the material to be tested. The test cell is then submerged in 1 liter of waste water from a chlorohydrin process, i.e., solutions having NaCl concentrations of 10 wt % and 20 wt %, respectively, at a temperature of between about 74° C. and about 81° C. and a pH of between about 11 and 12. Fluid motion of about 2 m/s is provided by a magnetic stirrer. Potentiostatic corrosion current density measurements at 150, 200, 300, 325, 350, 400 and 450 mV/Ag-AgCl were carried out for a time period of 1 hour. The results from this Example are summarized in FIGS. 2-4.

Figure 2:
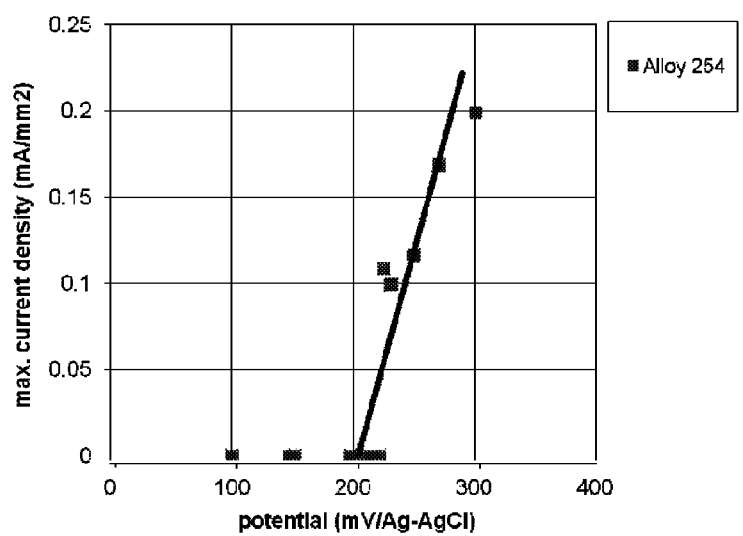
FIG. 2 is a graphical depiction of the effect of applied potentials on local corrosion current densities of 254 SMO in 10 wt % salt solution.
Figure 3:
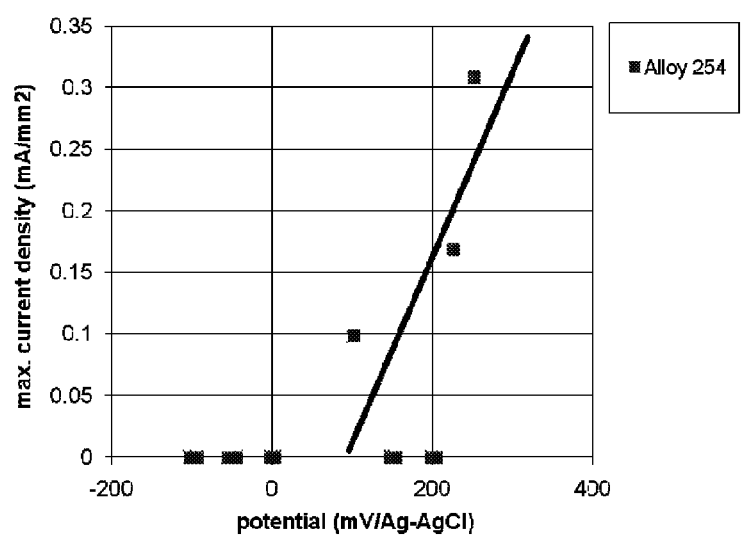
FIG. 3 is a graphical depiction of the effect of applied potentials on local corrosion current densities of 254 SMO in 20 wt % salt solution.
Figure 4:
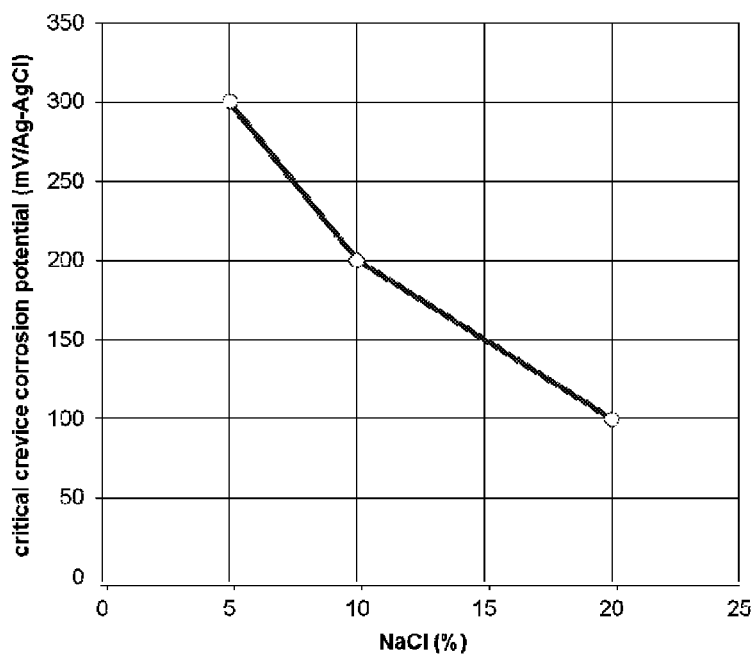
FIG. 4 is a graphical summary of the data shown in FIGS. 1-3.

As shown in FIG. 2, 254 SMO® exhibited no corrosion, i.e., exhibited a maximum current density (mA/mm$^2$) of approximately 0, up to an applied oxidation potential of about 200 mV/Ag-AgCl in 10 wt % solution of NaCl. In 20 wt % NaCl, 254 SMO® exhibited no corrosion, i.e., exhibited a maximum current density (mA/mm$^2$) of approximately 0, up to an applied potential of about 100 mV/Ag-AgCl (FIG. 3). The data shown in FIGS. 2 and 3, as well as the potential data from Example 1 are summarized and shown in FIG. 4. As shown in FIG. 4, at higher salt concentrations, lower critical potentials are required for the initiation of corrosion of 254 SMO®.

EXAMPLE 3

Figure 5:
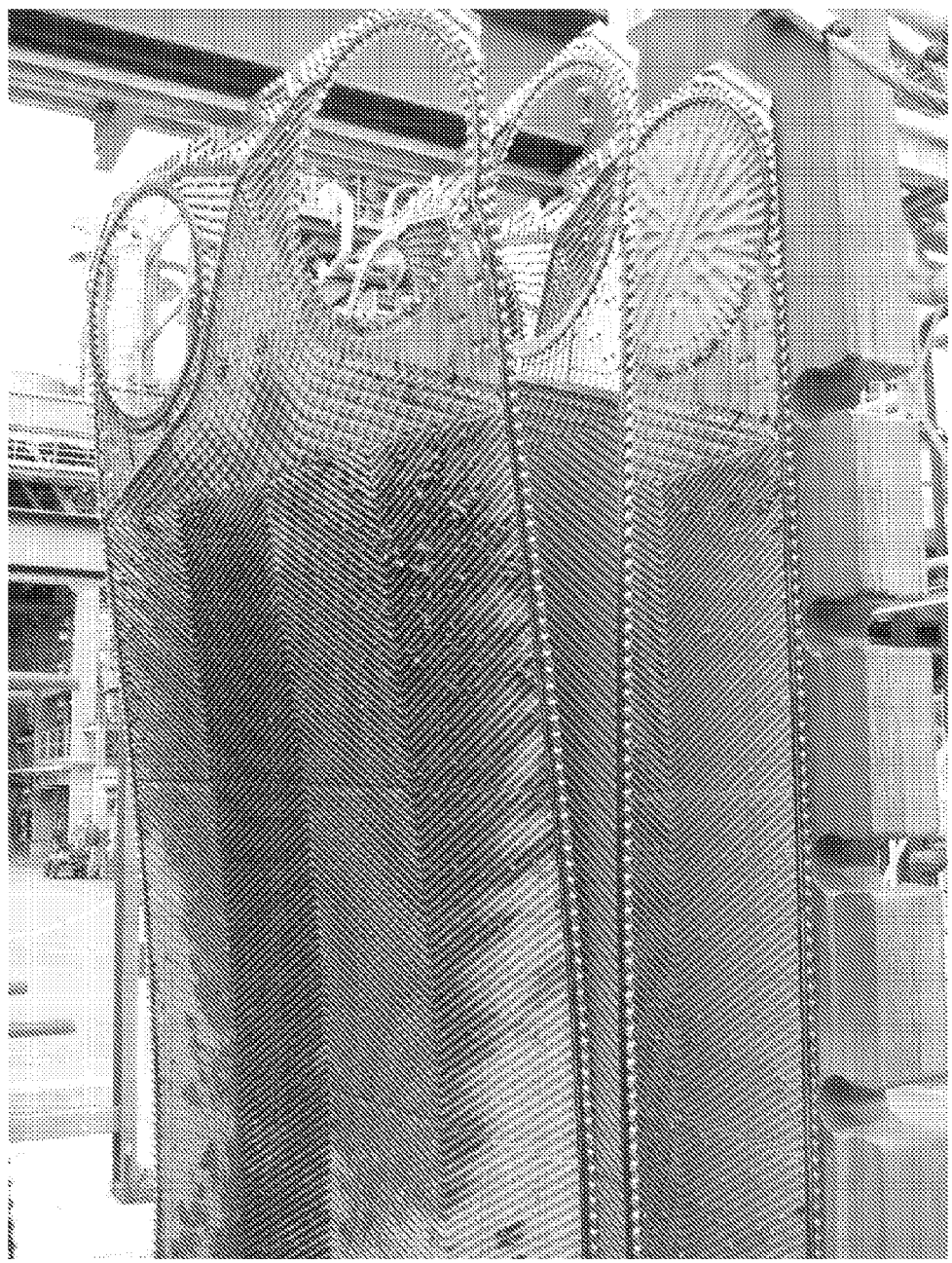
FIG. 5 is a photograph of individual plates removed from a heat exchanger after being exposed to a chlorohydrin process stream.
Figure 6:
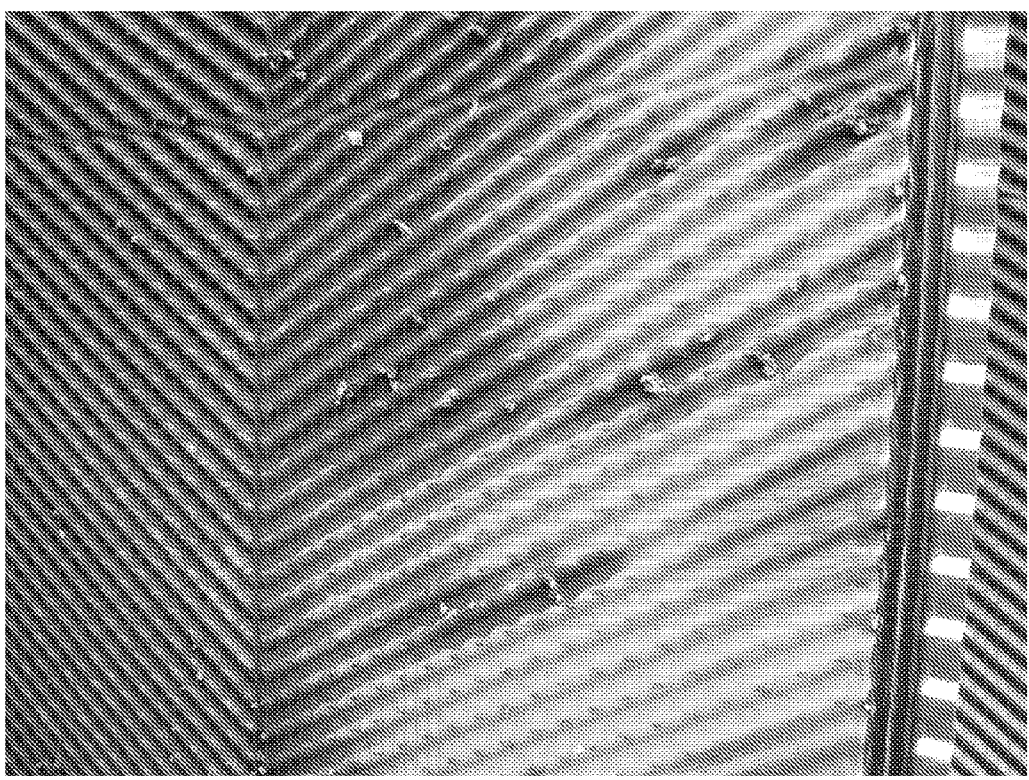
FIG. 6 is a photograph of individual plates removed from a heat exchanger after being exposed to a chlorohydrin process stream

To demonstrate the feasibility of the use of 254 SMO® under real conditions, a long-term test on an industrial scale is conducted. For this example, a plate and frame heat exchanger comprising plates made from 254 SMO® was tied into the waste water stream of an operating chlorohydrin process. After 16 months of operation at a temperature of 75 to 80° C., pH between 10.5 an 11, NaCl concentrations between 5 an 5.3 wt % and oxidizing potentials of up to +200 mV, no evidence of corrosion or crevice corrosion were observed on the 254 SMO® plates. In FIGS. 5 and 6, the intact plates after opening of the exchanger are shown. Blank spots indicate direct contact between adjacent plates, where no deposits could form. Although there are still some deposits from the process fluid on the plate surface, even these susceptible areas do not show crevice corrosion and the metal remains intact.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A process for the production of a chlorohydrin comprising
   generating a chlorohydrin process stream; and
   contacting at least a portion of a surface comprising a austenitic stainless steel comprising from about 0.18 wt % to about 0.52 wt % nitrogen, from about 19.5 wt % to about 24.5 wt % chromium, from about 17.5 wt % to about 22.5 wt % nickel, from about 6.0 wt % to about 7.5 wt % molybdenum, from about 0.01 wt % to about 0.02 wt % carbon, with the remainder being incidental impurities and the balance iron, with the chlorohydrin process stream.

2. The process of claim 1, wherein the chlorohydrin process stream has a pH of greater than about 9.

3. The process of claim 1, wherein the chlorohydrin process stream has a salt concentration of at least about 5 wt %.

4. The process of claim 1, wherein the chlorohydrin process stream has a temperature of at least about 70° C.

5. The process of claim 1, wherein the chlorohydrin process stream has an oxidation potential of up to about 300 mV/Ag-AgCl.

6. The process of claim 1, wherein the chlorohydrin process stream is a waste stream.

7. The process of claim 1, wherein the stainless steel comprises from about 0.18 wt % to about 0.22 wt % nitrogen, from about 23.5 wt % to about 24.5 wt % chromium, from about 21.5 wt % to about 22.5 wt % nickel, from about 6.0 wt % to about 6.5 wt % molybdenum, and from about 0.01 wt % to about 0.02 wt % carbon.

8. The process of claim 1, wherein the stainless steel comprises from about 0.48 wt % to about 0.52 wt % nitrogen, from about 19.5 wt % to about 20.5 wt % chromium, from about 17.5 wt % to about 18.5 wt % nickel, from about 7.1 wt % to about 7.5 wt % molybdenum, and from about 0.01 wt % to about 0.02 wt % carbon.

9. The process of claim 1, wherein the surface comprises a portion of a heat exchanger.

10. The process of claim 1, wherein the chlorohydrin produced is epichlorohydrin.

11. The process of claim 10, wherein the epichlorohydrin is produced by reacting allyl chloride with chlorine in the presence of water to form glycerol dichlorohydrin and treating the glycerol dichlorohydrin with a base to provide the epichlorohydrin.

12. The process of claim 10, wherein the epichlorohydrin is produced by reacting glycerol with hydrochloric acid to form glycerol dichlorohydrin and treating the glycerol dichlorohydrin with a base to provide the epichlorohydrin.

13. The process of claim 10, wherein the epichlorohydrin is produced by reacting allylalcohol dissolved in hydrochloric acid with gaseous chlorine to form glycerol dichlorohydrin and treating the glycerol dichlorohydrin with a base to provide the epichlorohydrin.

* * * * *